United States Patent [19]

Nelson

[11] 4,333,883
[45] Jun. 8, 1982

[54] PREPARATION OF N-CHLOROTHIO(METHYL)CARBAMOYL HALIDES

[75] Inventor: Stephen J. Nelson, Kalamazoo, Mich.

[73] Assignee: The Upjohn Company, Kalamazoo, Mich.

[21] Appl. No.: 280,638

[22] Filed: Jul. 6, 1981

[51] Int. Cl.³ .................... C07C 51/62; C07C 125/03
[52] U.S. Cl. ................................................ 260/544 C
[58] Field of Search .................................. 260/544 C

[56] References Cited

U.S. PATENT DOCUMENTS 3,699,163  10/1972  Kohn ............................... 260/544 C

FOREIGN PATENT DOCUMENTS 1931054   1/1971  Fed. Rep. of Germany.
2023079  11/1971  Fed. Rep. of Germany ... 260/544 C Primary Examiner—Natalie Trousof
Assistant Examiner—Frederick W. Pepper
Attorney, Agent, or Firm—Sidney B. Williams, Jr.

[57] ABSTRACT

A process for the preparation of N-chlorothio(methyl)-carbamoyl halides.

11 Claims, No Drawings

PREPARATION OF N-CHLOROTHIO(METHYL)CARBAMOYL HALIDES

DESCRIPTION

FIELD OF THE INVENTION

This invention relates to a novel process for preparing N-chlorothio(methyl)carbamoyl halides.

BACKGROUND OF THE INVENTION

N-chlorothio(methyl)carbamoyl halides have been shown to be useful as an intermediate for the preparation of certain pesticidal compounds. For example, U.S. Pat. Nos. 4,066,689, 4,058,549, 4,091,016 and 4,234,521 teach the use of N-chlorothio(methyl)carbamoyl halides for the preparation of insecticidal N-methyl(thio) substituted carbamates.

A procedure for the preparation of N-chlorothio(methyl)carbamoyl fluoride is reported in German Pat. Nos. 1,931,054 and 2,023,079 and is represented by reaction Chart A. The yield of product in this sequence is low, thereby reducing the utility of the title compound in preparing pesticidal compounds.

BRIEF SUMMARY OF THE INVENTION

The process involves (a) reacting an N-methylcarbamoyl halide with sulfur dichloride; (b) chlorinating the mixture formed in (a) to obtain a product containing N-chlorothio(methyl)carbamoyl halide and sulfur dichloride; and (c) subjecting the product obtained in (b) to distillation.

DETAILED DESCRIPTION OF THE INVENTION

The present invention is a process for preparing N-chlorothio(methyl)carbamoyl halide and can be represented schematically by Scheme B wherein halide is chloride or fluoride. In Step (a), the reaction of methylcarbamoyl halide with sulfur dichloride, it has been found that in order to achieve rapid and complete conversion of the starting material to product an excess of from twenty to three hundred percent (20-300%), preferably fifty to one hundred percent (50-100%), of sulfur dichloride is required.

The reaction is conducted in the presence of a suitable tertiary organic base as acid scavenger with or without a solvent at a temperature of between −50 and 35, preferably −20 and 10 for a period of between 0.1 and 3 hours. The reaction may be conducted in the presence of an inert solvent or without solvent, preferably without solvent. Suitable solvents include methylene chloride, ether, toluene, chlorobenzene, tetrahydrofuran and the like. The preferred solvents are methylene chloride and ether.

Suitable tertiary organic bases include trialkylamine, pyridine and 2,4-lutidine. The preferred tertiary organic base is 2,4-lutidine.

The crude product obtained in Step 1 contains significant amounts of sulfur monochloride which can interfere with the subsequent reaction. It has been found that the boiling point of sulfur monochloride and N-chlorothio carbamoyl fluoride are similar and separation by distillation is difficult. The sulfur monochloride can be removed and the desired product purified by first chlorination of the sulfur monochloride to the much more volatile sulfur dichloride, followed by distillation.

Chlorination, Step (b), is accomplished by reacting the crude product obtained in Step (a) with sulfuryl chloride or chlorine gas. The preferred chlorinating agent is chlorine gas.

The distillation, Step (c), is conducted at a temperature of about 40° C. to 80° C. and a pressure of about 10 mm to 100 mm.

In the case where a solvent is used, the precipitated amine hydrochloride is removed by filtration and the solvent removed under reduced pressure. The crude product thus obtained is treated with chlorine and then distilled.

Where no solvents are employed, the crude product is obtained by evaporative distillation directly from the amine hydrochloride salt. The crude product thus obtained is purified in the same fashion as described above.

Illustrative examples of the improved process follow. They are indicative of the scope of this invention and are not to be construed as limitative.

The process of this invention offers advantages over the process in which sulfur monochloride is utilized. One is that the yield is increased from thirty-four percent (34%) to seventy percent (70%).

EXAMPLE 1

N-Chlorothio(methyl)carbamoyl fluoride (Reaction without solvent)

A mixture of sulfur dichloride (86.9 g, 0.844 mol) and methylcarbamoyl fluoride (32.5 g, 0.422 mol) is cooled in an ice-salt bath (−15°). Using a hydraulically driven syringe, 2,4-lutidine (45.2 g, 0.422 mol) is added through a polyethylene tube below the surface of the reaction mixture at a rate to maintain a reaction temperature of +5-10° (24 min.). After the addition, the slurry is stirred at 15°-20° for 80 minutes then placed on a rotary evaporator at ∼100 mm with a bath temperature of 30°. After most of the excess sulfur dichloride has been removed, the bath temperature is increased to 80° and the pressure decreased to 10-20 mm to give 65.4 g of crude product.

Approximately 10 µl of diisopropylamine is added at once to a solution of 2-5 µl of the crude product in ether. The precipitated salts are filtered and the filtrate analyzed by gas chromatography which indicates 32% $S_2Cl_2$ by weight and 1% $SCl_2$. Chlorine is bubbled through the product until 11 g has been absorbed. The mixture is placed under 60 mm P and 30° for 15 minutes, then distilled to give N-chlorothio(methyl)carbamoyl fluoride (42.3 g, 69.8%) as a yellow liquid bp 54°-6°, 40 mm.

Utilizing a procedure similar to that used in Example 1 but substituting methylcarbamoyl chloride for methylcarbamoyl fluoride, there is obtained N-chlorothio(methyl)carbamoyl chloride.

EXAMPLE 2

N-Chlorothio(methyl)carbamoyl fluoride (Use of a solvent)

A mixture of sulfur dichloride (43.5 g, 422 mol) and N-methylcarbamoyl fluoride (16.3 g, 0.211 mol) in ether (200 ml) is cooled in an ice bath. A solution of 2,4-lutidine (22.6 g, 0.211 mol) in ether (50 ml) is added over 20 min. at a rate to maintain a reaction temperature of 5°-10° C. After the addition the mixture is stirred for 30 min. then filtered. The filtrate is carefully concentrated at 200 mm with a bath temperature of less than 25°. The crude product is analyzed and purified as in Example 1 to yield N-chlorothio(methyl)carbamoyl fluoride.

Utilizing a procedure similar to that used in Example 2 but substituting N-methylcarbamoyl chloride for N-methylcarbamoyl fluoride there is obtained N-chlorothio(methyl)carbamoyl chloride.

CHART A

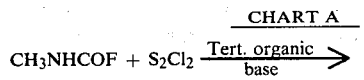

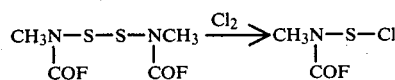

CHART B

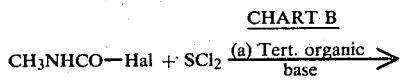

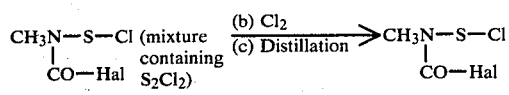

I claim:

1. A process for preparing a N-chlorothio(methyl)carbamoyl halide which comprises (a) reacting N-methylcarbamoyl halide with an excess of sulfur dichloride in the presence of a tertiary organic base to form a mixture containing N-chlorothio(methyl)carbamoyl halide and sulfur monochloride; (b) chlorinating the mixture obtained in (a) to obtain a product containing N-chlorothio(methyl)carbamoyl halide and sulfur dichloride and (c) subjecting the product obtained in (b) to distillation.

2. A process according to claim 1 wherein the excess of sulfur dichloride is twenty to three hundred percent.

3. A process according to claim 2 wherein the excess of sulfur dichloride is fifty to one hundred precent.

4. A process according to claim 2 or 3 wherein the tertiary organic base is 2,4-lutidine.

5. A process according to claim 2 or 3 conducted in the presence of a solvent.

6. A process according to claim 2 or 3 conducted in the absence of a solvent.

7. A process according to claim 1 wherein the chlorinating agent is chlorine gas.

8. A process according to claim 6 wherein the chlorinating agent is chlorine gas.

9. A process according to claim 1 wherein the chlorinating agent is sulfuryl chloride.

10. A process according to claim 6 wherein the chlorinating agent is sulfuryl chloride.

11. A process according to claim 7 wherein N-methylcarbamoyl fluoride is utilized in step (a) and the product prepared is N-chlorothio(methyl)carbamoyl fluoride.

* * * * *